US012653811B2

(12) United States Patent
Richards et al.

(10) Patent No.: US 12,653,811 B2
(45) Date of Patent: Jun. 16, 2026

(54) DOSAGE REGIMEN OF AMLODIPINE

(71) Applicant: CLOSED LOOP MEDICINE LTD, Babraham (GB)

(72) Inventors: Andrew John McGlashan Richards, Babraham (GB); Paul Goldsmith, Babraham (GB); David Collier, Babraham (GB); David Cox, Babraham (GB); Bruce Campbell, Babraham (GB)

(73) Assignee: CLOSED LOOP MEDICINE LTD, Babraham (GB)

( * ) Notice: Subject to any disclaimer, the term of this patent is extended or adjusted under 35 U.S.C. 154(b) by 673 days.

(21) Appl. No.: 17/923,641

(22) PCT Filed: May 7, 2021

(86) PCT No.: PCT/GB2021/051112
§ 371 (c)(1),
(2) Date: Nov. 7, 2022

(87) PCT Pub. No.: WO2021/224641
PCT Pub. Date: Nov. 11, 2021

(65) Prior Publication Data
US 2023/0181551 A1 Jun. 15, 2023

(30) Foreign Application Priority Data
May 7, 2020 (GB) ..................................... 2006819

(51) Int. Cl.
*A61K 31/4422* (2006.01)
*G16H 20/10* (2018.01)
*G16H 50/20* (2018.01)

(52) U.S. Cl.
CPC ......... *A61K 31/4422* (2013.01); *G16H 20/10* (2018.01); *G16H 50/20* (2018.01)

(58) Field of Classification Search
CPC .............................. A61K 31/4422; A61P 9/12
See application file for complete search history.

(56) References Cited

U.S. PATENT DOCUMENTS

| | | | | |
|---|---|---|---|---|
| 6,057,344 A * | 5/2000 | Young | .................... | A61K 31/44 514/356 |
| 6,162,802 A * | 12/2000 | Papa | ...................... | A61K 31/55 514/212.07 |
| 11,096,595 B2 * | 8/2021 | Albadawi | .............. | A61B 5/742 |
| 2003/0022922 A1 * | 1/2003 | Lemmens | .............. | A61K 31/44 514/355 |
| 2004/0254176 A1 | 12/2004 | Grigorieff et al. | | |
| 2008/0027291 A1 | 1/2008 | Williams-Hartman | | |

FOREIGN PATENT DOCUMENTS

JP       2006-306754 A     11/2006

OTHER PUBLICATIONS

Webb (https://www.pmsinstruments.co.uk/blog/pms-algorithm-for-blood-pressure-measurement/, Jul. 2014). (Year: 2014).*
Ombani (Frontiers in Cardiovascular Medicine, 2019, 6, 40, p. 1-7). (Year: 2019).*
International Preliminary Report on Patentability dated Nov. 8, 2022 from corresponding International (PCT) Patent Application No. PCT/GB2021/051112, 8 pages.
Frick et al.; "Amlodipine: A Double-Blind Evaluation of the Dose-Response Relationship in Mold to Moderate Hypertension", Journal of Cardiovascular Pharmacology, vol. 12 (Suppl. 7), 1988, pp. S76-S78.
Mukherjee et al.; "Guiding dose adjustment of amlodipine after co-administration with ritonavir containing regimens using a physiologically-based pharmacokinetic/pharmacodynamic model", Journal of Pharmacokinetics and Pharmacodynamics, 2018, 45:443-456.
Murdoch et al.; "Amlodipine A Review of its Pharmacodynamic and Pharmacokinetic Properties, and Therapeutic Use in Cardiovascular Disease", Drugs, Adis International Ltd., vol. 41 (3) 1991, pp. 478-505.
Osterloh, Ian; "The safety of amlodipine", American Heart Journal, vol. 118, No. 5, Part 2, Nov. 1989, pp. 1114-1120.
International Search Report dated Aug. 25, 2021 from corresponding International (PCT) Patent Application No. PCT/GB2021/051112, 4 pages.
Written Opinion dated Aug. 25, 2021 from corresponding International (PCT) Patent Application No. PCT/GB2021/051112, 7 pages.
Amlodipine Patient Insert Leaflet NDA 19-787/S-042, 14 pages.
Donnelly et al., Pharmacodynamic modelling of the antihypertensive response to amlodipine, Clinical Pharmacology & Therapeutics, Oct. 1993, pp. 303-310.
FDA Amlodipine Approval Clinical Pharmacology and Biopharmaceutical Review (2002), NDA 19-787/S30, 36 pages.
Heo et al.; "Quantitative model for the blood pressure lowering interaction of valsartan and amlodipine"; Br J Clin Pharmacol (2016), 82, 1557-1567.
Williams et al.; "Amlodipine Pharmacokinetics in Healthy Volunteers"; J Clin Pharm (1988), 28, 990-994.
Japanese Notice of Reasons for Refusal dated Mar. 18, 2025 from corresponding Japanese Patent Application No. 2022-566669, 12 pages.
Kai, Hisashi; "Timing of increasing or decreasing antihypertensive medication"; Medicina, 2016, vol. 53, No. 11, pp. 1784-1788.
Makino et al.; "Efficacy of carvedilol in patients with chronic heart failure", Medical Treatment and New Drugs, vol. 40, No. 7, Jul. 2003, 10 pages.
Sugimoto, Koichi; "How to use antihypertensive drugs", Medical Online, Resident Note, vol. 9, No. 6, Sep. 2007, pp. 799-808.
Ura et al.; "A review of current hypertension treatments", Circulation Control, vol. 25, No. 2, 2004, pp. 108-113.

* cited by examiner

*Primary Examiner* — Umamaheswari Ramachandran
(74) *Attorney, Agent, or Firm* — Ruggiero McAllister & McMahon LLC

(57) ABSTRACT

There is a dosage regimen for amlodipine for use in the treatment of hypertension.

22 Claims, 8 Drawing Sheets

DOSAGE REGIMEN OF AMLODIPINE

CROSS-REFERENCE TO RELATED APPLICATIONS

The present application claims priority from PCT Application No. PCT/GB2021/051112, filed May 7, 2021, which claims priority from British Patent Application No. 2006819.3, filed May 7, 2020, the disclosure of which are incorporated herein in their entireties.

FIELD OF THE DISCLOSURE

This disclosure relates to a dosage regimen for amlodipine for use in the treatment of hypertension.

BACKGROUND OF THE DISCLOSURE

Hypertension is the leading preventable cause of premature death worldwide. Globally, 1.39 bn people are estimated to have hypertension, and it caused≈10.7 million deaths in 2015. It is projected to affect more than 1.5 billion people around the world by 2025.

In the UK ~30% of adults have hypertension; 9.5 m have a diagnosis, and a further 5 m people in England alone may have hypertension yet be unaware. The annual incidence of new cases is 5-8%. Physician inertia (inadequate up-titration of treatment, especially from monotherapy) and poor patient adherence to treatment (especially when based on multiple pills) are now recognised as major factors contributing to poor BP control.

Amlodipine is a long acting dihydropyridine calcium channel blocker and exerts its action by the inhibition of calcium influx into vascular smooth muscle decreasing peripheral vascular resistance and is used in the treatment of hypertension and stable angina. It is one of the most commonly prescribed drugs for hypertension with over 75 million prescriptions written in the USA alone in 2017.

The drug is well absorbed (90%) and because of its long half-life (ca. 30-60 h), it is typically administered once a day at approved doses. The current approved dosages are 2.5, 5.0, and 10.0 mg per day.

The drug is slowly absorbed. Typically, peak levels after a single dose are seen approximately eight hours after the first dose, although this can vary between 6 and 9 hours.

Maximum levels are typically not reached for 5 to 8 days due to a three-fold accumulation after initiation of therapy when maximal effectiveness is produced.

Unfortunately, the time to reach this steady-state and the extent of the accumulation varies from one subject to another. Therefore, it is not a simple matter to predict whether a particular dose is suitable for a particular subject.

At steady-state it has been shown that there is a variance in the average amlodipine blood levels of up to 30% between subjects at the same dose. In addition, there is a variance of approximately 25% from peak levels to trough levels over a 24-hour period before the next doses taken.

Thus, for any one subject there can be a total kinetic difference of more than 50%. This essentially means that for a given response, one subject will respond well at a dose of 4 mg, whilst another will be better treated with a dose of 2 mg irrespective of the differences in pharmacodynamic response and the issues of adverse effects. Therefore, finding the best dose of amlodipine for a particular patient is highly desirable, not least because unwanted side effects is a contributing factor to patient compliance.

In addition to the normal pharmacokinetic variability described above, the variability is particularly high in the elderly, where the elimination half-life can vary from 50-90 hours with a resulting increase in the total exposure of up to 60%.

Similarly, comorbid diseases can affect the kinetics of amlodipine. For example, liver disease and heart failure can reduce the clearance and thus markedly increase circulating plasma levels.

Thus, the plasma concentrations of amlodipine alone can vary greatly from one subject to another even when they are on the same dose, and without measuring these concentrations it is not possible to monitor the effect of these differences on a day-to-day basis.

The use of daily monitoring and recording would allow these individual differences to be assessed.

The lowering of blood pressure has been shown to be directly related to circulating plasma levels (Donelly et al. 2002). Thus, the variable pharmacokinetics of amlodipine has a profound influence on its effectiveness and variations in the kinetic parameters from one individual to another will change the response accordingly.

This relationship can be shown using different mathematical models based on linear and non-linear pharmacokinetic/pharmacodynamic relationships. A number have been proposed but examples of three are shown below:

| | | |
|---|---|---|
| $SBP = 134 + 4.85(sex) - 1.22(C)$ | linear Model | FDA |
| $SBP = 119(1 - 0.164(C/C + 8.24)$ | non-linear model | Heo |
| $SBP = SBP_0 - 3.1.Cexp(-0.52.t)$ | non-linear model | Donnelly |

Where SBP=Systolic Blood Pressure: sex=1 for males 0 for females; C=plasma amlodipine concentration; t=time after dosing; $SBP_0$=baseline BP It is therefore possible using these population models to compute the antihypertensive effect of amlodipine for any given plasma concentration and allows modelling of the effectiveness the drug over a wide range of different doses. This requires samples to be taken from a patient and then analysed in a laboratory.

The listing or discussion of an apparently prior-published document in this specification should not necessarily be taken as an acknowledgement that the document is part of the state of the art or common general knowledge.

SUMMARY OF THE DISCLOSURE

The present inventors have surprisingly and unexpectedly found that precision dosing of amlodipine can deliver reductions in blood pressure in patients with hypertension. The relationship between dose and blood pressure may be used to provide information on a proposed dosage regimen.

As will be evident from the data and information presented below, the administration of amlodipine according to the specific dosage regimen described herein, makes it possible to both reduce side effects and better control blood pressure in the patient. For example, administering amlodipine according to the specific dosage regimen of the present disclosure may significantly reduce, or even completely eliminate, adverse effects that may include oedema, dizziness, flushing, palpitations and fatigue.

In a first aspect, the present disclosure provides amlodipine, for use in the treatment of hypertension in a patient, wherein the dosage regimen comprises:

i. for a period of at least 5 days:
    a) administering an initial daily dose of between 0 mg
      and 10 mg amlodipine to the patient;
    b) indicating that the patient's blood pressure readings
      are recorded on at least 3 separate days, using a
      blood pressure device;
    c) indicating that any side-effects experienced by the
      patient are recorded on at least 3 separate days
ii. increasing or decreasing (if not already 0 mg) the daily
    dose of amlodipine by between 1 mg and 2.5 mg, or
    maintaining the daily dose of amlodipine, based on the
    blood pressure readings and the patient reported side-
    effects; and
iii. repeating steps (i) and (ii) with either the increased,
    decreased or maintained dose replacing the initial daily
    dose in step (a) for a number of times until a specified
    patient treatment period has elapsed or until a target
    blood pressure is reached.

In a second aspect, a method for the treatment of hypertension in a patient in need thereof comprises administering amlodipine to the patient according to the dosage regimen described above.

In a third aspect, a method for producing an amlodipine dosage regimen for a patient, comprises recording the patient's blood pressure on at least 3 separate days and calculating a moving average of the blood pressure, using a blood pressure device, and recording any side-effects experienced by the patient, on at least 3 separate days, and producing an amlodipine dosage regimen based on the moving average of the blood pressure readings and the patient reported side-effects.

Certain steps of the methods described above may be carried out on software executed on an electronic device.

In a fourth aspect, a composition comprises amlodipine and pharmaceutically acceptable excipients, wherein the amount of amlodipine in the composition is 1 mg, 2 mg, 3 mg, 4 mg, 6 mg, 7 mg, 8 mg 9 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg or 30 mg.

These uses and methods are hereinafter referred to as the uses and methods of the disclosure.

DETAILED DESCRIPTION OF THE DISCLOSURE

Figure 1:
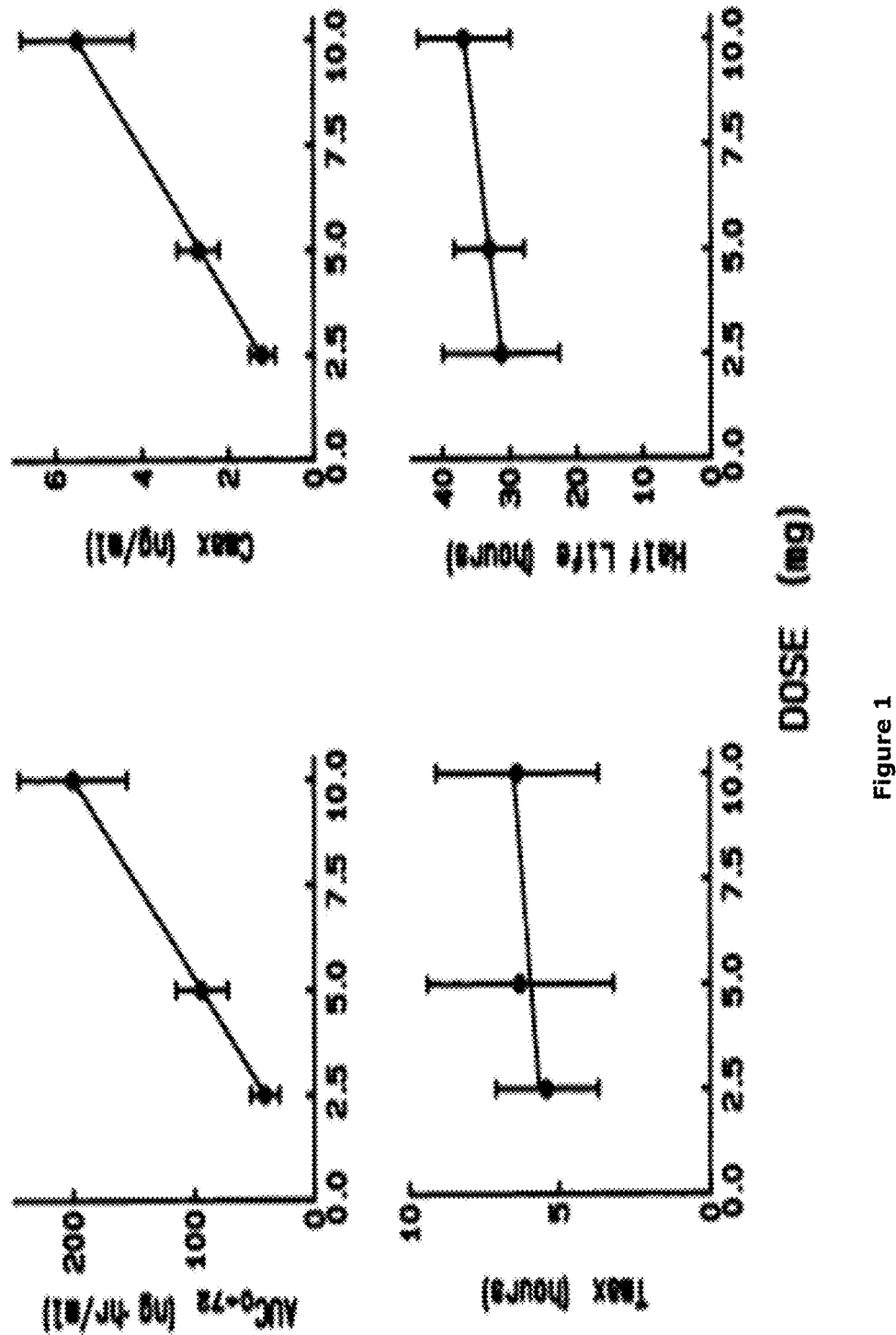
FIG. 1. Linear Relationships Between PK parameters and Dose (Williams et al 1988)

Typically, the uses and methods described above may be used to treat patients if they have had a diagnosis of hypertension according to national guidelines, preferably according to NICE/BIHS CG127 criteria, any updates thereof, or similar national or international hypertension guidelines, and preferably wherein they have already conducted 24 h ambulatory blood pressure monitoring (ABPM) recording or home blood pressure monitoring.

In a preferred embodiment, step b) includes a determination of a moving average of the blood pressure readings and the increasing, decreasing or maintaining in step (ii) is based on the moving average of the blood pressure. The moving average is preferably a 3-day moving average. Those 3 days are preferably, but not necessarily, consecutive, i.e. Monday, Tuesday and Wednesday.

In a preferred embodiment, the readings used to calculate the moving average are taken at about the same time each day, for example upon waking or upon going to bed. This is advantageous because it gives a more accurate picture of blood pressure variation and minimises any effects from diurnal variation in blood pressure. Diurnal blood pressure variation is very common in the general population.

It is a requirement of the disclosure that the period in step (i) is at least 5 days. It is also a requirement that readings are recorded on at least 3 separate days. Therefore, readings could be taken on days 1, 2 and 3, or on days 1, 2 and 4, or on days 1, 2 and 5, or on days 2, 3 and 4, and so on. In whichever permutation, there will enough readings to include a 3-day moving average. It is preferred that blood pressure readings are taken daily (preferably at the same time each day) and it is preferred that the 3-day moving average is calculated over consecutive days.

The moving average is the preferred way to measure blood pressure because it gives a more accurate picture of how blood pressure is changing over time and minimises the effect of unusually high or low readings.

In some embodiments, the period in step (i) is either pre-determined or is determined by the time taken to reach less than 10% variability (more preferably less than 7% variability) in the moving average blood pressure. This may mean that a steady state has been reached for blood pressure and therefore a determination can be made on whether to vary the dose.

In step (i) of the uses and methods described above, the pre-determined period may be at least 7 days. For example, the predetermined period may be at least 10 days, at least 14 days or at least 21 days. The predetermined period may be from about 5 days to about 21 days, or from about 7 days to about 14 days.

The initial daily dose may be determined based on a patient's medical history and/or history of prior side-effects when taking amlodipine.

Typically, the daily dose in step (i) is determined by a physician or delegated health care professional. It may also be determined automatically by software executed on a computer.

The determination may include a review of a patient's blood pressure.

The daily dose in step (i) may be 0 mg, 1 mg, 2 mg, 2.5 mg, 3 mg, 4 mg, 5 mg, 6 mg, 7 mg 8 mg, 9 mg or 10 mg of amlodipine.

In step (i) of the uses and methods described above, the patients' blood pressure is recorded at least every other day during the predetermined period in step (i). For example, the patients' blood pressure may be recorded at least every day, at least twice a day, at least three times a day or at least four times a day. In a preferred embodiment, the patients' blood pressure is recorded once a day, generally at about the same time each day.

It is desirable that the patients' blood pressure is recorded as often as is reasonable. The more often that the blood pressure readings are taken, the more data points are provided allowing for a more accurate determination of the moving average blood pressure of the patient. The blood pressure may be recorded every other day, every day or twice a day.

This is because BP is a continuous variable that fluctuates constantly in response to various changes in physical and mental activities, sleep, and autonomic, humoral, mechanical, myogenic and environmental stimuli.

As such, clinic BP or home BP (HBP) in patient at one time can be considerably different from his/her average day and night-time BP. This presents a challenge in diagnosing and prescribing treatments for patients correctly.

Thus, it may be preferred that the blood pressure readings are taken at the same time each day, for example in the morning and evening, such as at least 30 minutes after waking and at least 30 minutes before bed.

It may also be preferred that the blood pressure readings are taken at least 30 minutes after an activity that may cause a fluctuation in the blood pressure of the patient. For example, the consumption of a meal, exercise or a hot bath/shower.

It may further be preferred that the blood pressure may be corrected to account for variances due to circadian rhythms.

The blood pressure readings may be taken using any suitable blood pressure device.

Examples of suitable blood pressure devices include, but are not limited to, blood pressure monitors, and exercise devices (such as exercise watches/fitbits). It is preferred that the same device is used for each reading.

In step (i) of the uses and methods described above, the blood pressure readings may be recorded on an electronic device, for example, on a computer, smartphone or tablet, such that the blood pressure readings may be electronically stored and/or passed to a physician or delegated health care professional.

The electronic device may be used by the patient and/or a physician or delegated health care professional.

The blood pressure readings may be transferred from the blood pressure monitor to the electronic device electronically, and preferably automatically.

In step (i) of the uses and methods described above, side effects including, but not limited to, oedema, palpitations, flushing and/or dizziness are recorded.

In step (i) of the uses and methods described above, the side effects are recorded at least every other day during the predetermined period in step (i). For example, the side effects may be recorded at least every day, at least twice a day, at least three times a day or at least four times a day.

In step (i) of the uses and methods described above, the side effects may be recorded at the same time each day, for example, they may be recorded in the morning or in the evening.

In step (i) of the uses and methods described above, the side effects may be recorded on an electronic device. For example, on a computer, smartphone or tablet, such that the side effects may be electronically stored and passed to a physician or delegated health care professional.

Side-effects of the uses and methods described above may include oedema, palpitations, flushing, dizziness, headache, swelling, skin reactions, abdominal pain, fatigue, drowsiness, nausea or vomiting, gum welling, constipation, muscle cramps or poor sleep.

The electronic device may be used by the patient and/or a physician or delegated health care professional.

Typically, the blood pressure readings obtained in step (i) and the side effects recorded in step (i) may be recorded on the same electronic device, enabling both sets of information to be stored and/or passed to a physician or delegated health care professional.

Step (i) may include an additional step, wherein in addition to the side effects being recorded, it is recorded whether the patient has taken the required daily dose of amlodipine.

In some embodiment, the time of day that the amlodipine was taken is recorded. The recording of whether the patient has taken the required daily dose of amlodipine may be done by the patient or may be recorded by an electronic device. For example, the electronic device may be electronic packaging that records when a tablet has been removed from the packaging.

In step (i) of the uses and methods described above, a moving average of the blood pressure readings is determined.

The moving average blood pressure reading can then be used to determine whether the amlodipine dosage in step (i) is correct for the patient, and what, if any modifications to the dosage may be required.

The present inventors have surprisingly and unexpectedly found that this can be achieved by reviewing the determined moving average blood pressure readings, in combination with the patient reported side-effects. If the moving average blood pressure and patient reported side effects are analysed in combination with the dose, then a personalised dose/response curve can be created, for example such as that shown in FIG. 3. The dose/response curve may also be known as a dose/PD curve. This enables decisions to be made on whether to increase, decrease of maintain the amlodipine dose and allows for the determination of a personalised "therapeutic window" for a patient. This may be performed by a physician or healthcare professional or executed by software on a computer.

The increasing and decreasing of the amlodipine dose in step (ii) may include a comparison with a pre-determined control blood pressure level, which may be 135 mmHg systolic and 85 mmHg diastolic. The control blood pressure may be personalised for the patient and take into account age, sex, weight or pre-existing medical conditions.

The increasing and decreasing of the amlodipine dose in step (ii) may include a comparison with a dose/response curve, as described herein. In a preferred embodiment, the dose/response curve may have been personalised for the patient.

Figure 3:
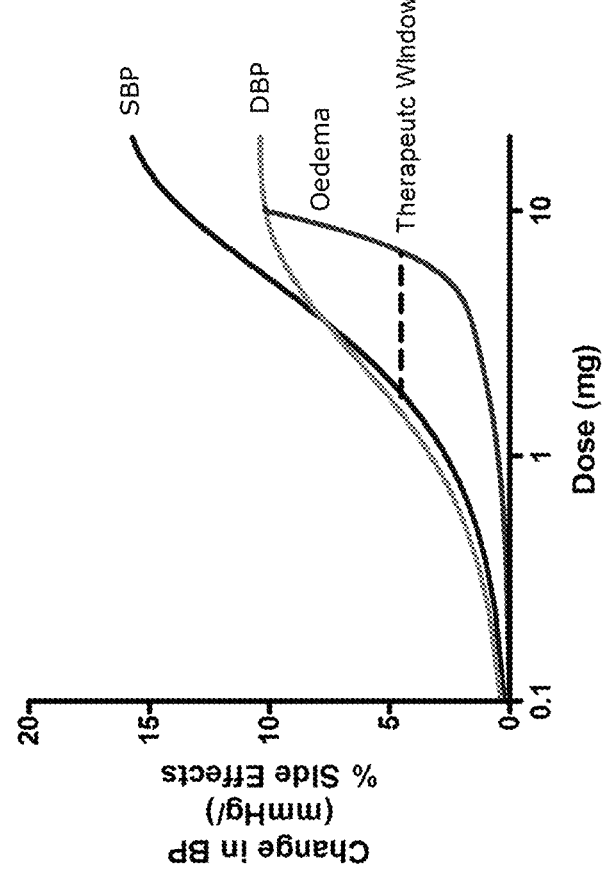
FIG. 3. Sigmoidal Emax model Plot for Dose/BP reduction showing Therapeutic Window FIG. 4. Flow Chart of Study FIG. 5. Flow Chart of Study FIG. 6. Mean blood pressure vs Dose titration graph from patients in the exemplary trial (n=number of patients, W=week, EOS=End of Study)

In some embodiments of the methods and uses of the disclosure, the comparison with a dose/response curve initially uses a standardised population dose/response curve, for example of the type shown in FIG. 3. Over time, and therefore as more blood pressure readings are taken from the patient at different doses, a personalised dose/response curve may be created and this can be used to determine the increase or decrease of the amlodipine dose producing an "Individualised Therapeutic Window". This may enable the selection of a dose for which there is a maximum BP effect for a minimum of side effects.

The pharmacokinetics (PK) of amlodipine is linear across a wide range of doses (see FIG. 1), and together with nonlinear models to measure the change in blood pressure, it is possible to compute an expected antihypertensive activity for any given dose, thus changing the doses for an individual patient upwards or downwards.

As discussed above, models have previously been generated to calculate the reduction in blood pressure from plasma concentrations, but there were no models available to calculate the BP reduction from dose.

However, the inventors have found that since the PK across the dosing range has been shown to be linear, it is thus possible to calculate population maximal steady state levels at any dose (Cmaxs's) by combining the PK dosing information with values for the steady state plasma levels of amlodipine concentrations which occur after, for example, a week or more of treatment. This principle (and the calculations described below) may be used to create either a standard or a personalised dose/response curve for use in the disclosure.

Using the Heo non-linear PKPD models for the change in systolic and diastolic BP after amlodipine together with the calculated plasma levels at each dose, it is possible to calculate the change from baseline in BP for any given dose of amlodipine using the following calculations, where C is the plasma concentration at any time.

$$SDP=119-(119*(1-(0.164*(C/C+8.24))$$

$$DBP=71.3-(71.3(1-(0.164*(C/C+2.97))$$

Figure 2:
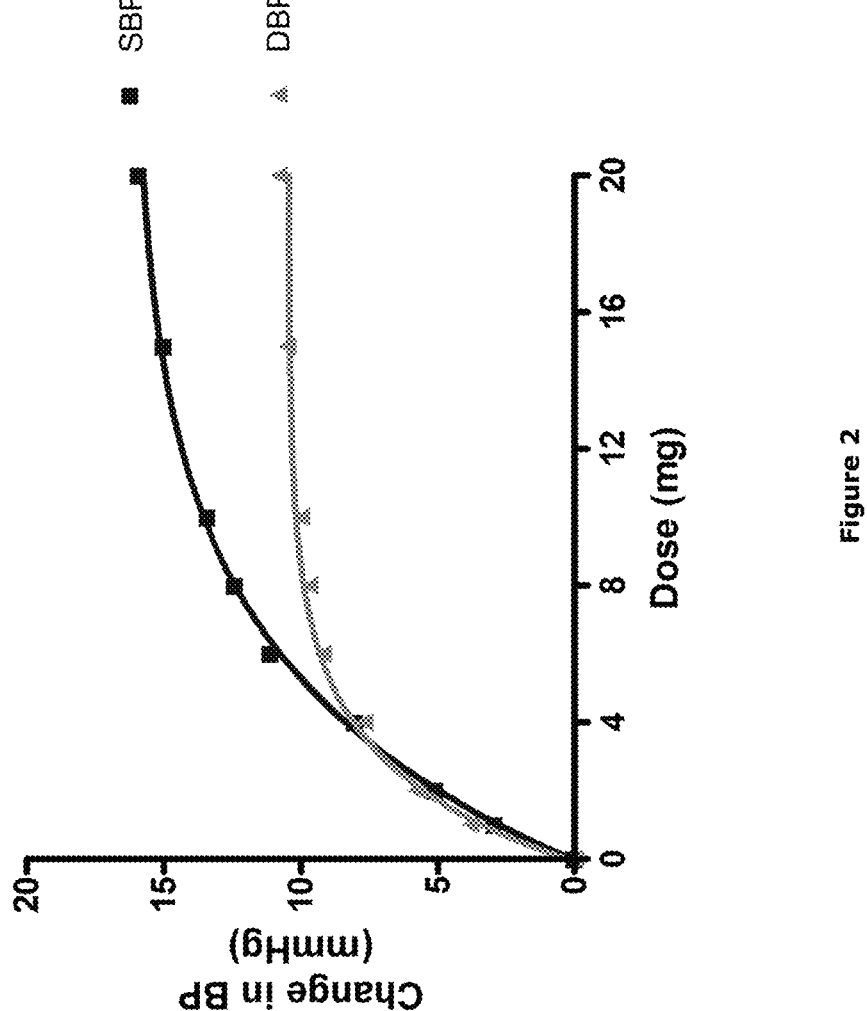
FIG. 2. Linear Dose response of Dose versus BP reduction

Population data points were calculated using published PK results, extrapolating across the range of plasma levels assuming PK linearity and then using the Heo model calculating the full dose/response (PKPD) BP curve. The results are shown in Table 1 and FIG. 2. This may be used as an initial starting model for each patient to adjust their dose up or down based on the increments shown.

TABLE 1

Calculated Population Amlodipine Steady State Levels and Resultant BP changes

| | Dose (mg) | | | | | | | |
|---|---|---|---|---|---|---|---|---|
| | 1 | 2 | 4 | 6 | 8 | 10 | 15 | 20 |
| $Cmax_{SS\ (ng/ml)}$ | 1.4 | 2.9 | 5.8 | 10.8 | 14.4 | 18.0 | 27.0 | 36.0 |
| SBP Reduction (mmHg) | 2.9 | 5.1 | 8.0 | 11.1 | 12.4 | 13.4 | 15.0 | 15.9 |
| DBP Reduction (mmHg) | 3.8 | 5.8 | 7.7 | 9.2 | 9.7 | 10.0 | 10.5 | 10.8 |

The above model may be used to create a dose/response curve and is an example of a dose/response curve that may be used in the present disclosure. This model may be used to choose the initial dose. The above model may also be used to modify the dose. Over time, and once several data points are collected, it may be possible to construct a personalised model based on the above general model. This allows for greater dose personalisation.

FIG. 3 shows the Sigmoidal E max plot for SBP and DBP using the data from Table 1.

The Dose/BP model and parameters are:

$$\Delta SBP=E0+(E\ max*D^N)/(EC50^N+D^N)$$

Where Emax=Maximal BP lowering effect, E0=effect at 0 dose (placebo) N=slope, D=Dose, EC50=Dose at 50% of maximal effect

TABLE 2

Dose/BP model Parameters

| | Systolic BP | Diastolic BP |
|---|---|---|
| Emax | 17.6 mmHg | 11.3 mmHg |
| E0 | 1.6 mmHg | 1.8 mmHg |

TABLE 2-continued

Dose/BP model Parameters

| | Systolic BP | Diastolic BP |
|---|---|---|
| EC50 | 4.9 mg | 2.6 mg |
| Slope N | 1.64 | 1.85 |

Based on this model it may be possible to calculate for any individual subject what would be their likely BP after a change in their dose upward or downwards.

Thus, in an aspect of the disclosure, the increasing or decreasing of the daily dose of amlodipine in step (ii) is calculated using the formulae:

$$\Delta SBP=E0+(E\ max*D^N)/(EC50^N+D^N),$$

wherein Emax=Maximal BP lowering effect, E0=effect at 0 dose (placebo) N=slope, D=Dose, EC50=Dose at 50% of maximal effect.

The above may be used to create a dose/response curve for use in the present disclosure.

It is envisaged that as the patient records blood pressure readings, and changes doses, these may be used in the above calculations to provide a patient specific control blood pressure.

Therefore, in a further aspect of the disclosure, the predetermined control may be based on the average blood pressure readings obtained in step (i).

Therefore, in a further aspect of the disclosure, the increasing or decreasing of the daily dose of amlodipine in step (ii) may be dependent on a Dose/response model that has been created specifically for a patient. For example, where the Dose/response model is based upon the rate of change of a patient's blood pressure for a given increase in amlodipine dose.

In the uses and methods described above, step (ii) may be carried out by software executed on an electronic device. For example, on a computer, smartphone or tablet. The electronic device may be used by the patient and/or a physician or delegated health care professional.

Steps (i) and (ii) may be repeated. For example, they may be repeated at least 3 times.

In some embodiments, the repeating of steps (i) and (ii) with either the increased, decreased or maintained dose replacing the initial daily dose in step (a) is for a number of times until a specified patient treatment period has elapsed or until a target blood pressure is reached.

The specified patient treatment period may be about 16 weeks.

The target blood pressure may be dependent on the individual patient and may take into account their history and other medical conditions.

In the uses and methods described above, the dose of amlodipine may not exceed 30 mg.

The amlodipine used in the uses and methods described above may be in the form of a liquid or a solid. Preferably, the amlodipine is in the form of a solid dosage formulation.

It is preferred that amlodipine used in the uses and methods described above is administered orally. For example, the amlodipine used in the uses and methods described above may be administered in a solid or liquid dosage formulation via the oral route.

Dosage forms for use in the present disclosure include tablets, capsules, suppositories, pellets, solutions, emulsions, aqueous or oily suspensions, syrups and elixirs or additional routes such as intranasal, inhalation, sublingual, or buccal.

The amlodipine used in the uses and methods described above may comprise amlodipine and pharmaceutically acceptable excipients, wherein the amount of amlodipine in the composition is 1 mg, 2 mg, 3 mg, 4 mg, 5 mg, 6 mg, 7 mg, 8 mg 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg or 30 mg.

An aspect of the disclosure (described above) is a composition comprising amlodipine, wherein the amount of amlodipine in the composition is 1 mg, 2 mg, 3 mg, 4 mg, 5 mg, 6 mg, 7 mg, 8 mg 9 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg or 30 mg. The composition may be formulated for oral administration. The composition may be in liquid form.

For the avoidance of doubt, in this specification when we use the term "comprising" or "comprises" we mean that the extract or composition being described must contain the listed ingredient(s) but may optionally contain additional ingredients. When we use the term "consisting essentially of" or "consists essentially of" we mean that the extract or composition being described must contain the listed ingredient(s) and may also contain small (for example up to 5% by weight, or up to 1% or 0.1% by weight) of other ingredients provided that any additional ingredients do not affect the essential properties of the extract or composition. When we use the term "consisting of" or "consists of" we mean that the extract or composition being described must contain the listed ingredient(s) only.

As used herein, the term "treatment" (and, similarly, "treating") takes its normal meaning in the field of medicine. In particular, the term may refer to achieving a reduction in the severity of one or more clinical symptom associated with the disease or disorder (e.g. the fungal infection), as may be determined using techniques known to those skilled in the art (for example, by a medical physician) and/or to slowing the progression of the disease or disorder (i.e. increasing the amount of time taken for the disease or disorder to progress to a more severe state, e.g. when compared to the time expected to be taken in a patient not so treated).

In one aspect the amlodipine is for use in the dosage regimen described herein as the only active agent administered during the dosage regimen, suitably amlodipine is the only active agent for use in treating hypertension administered during the dosage regimen. In one aspect, no other drugs aimed at lowering the blood pressure are administered during the dosage regimen. For example in one aspect olmesartan, chlorthalidone, statin, or Valsartan are not administered during the dosage regimen.

For the avoidance of doubt, preferences, options, particular features and the like indicated for a given aspect, feature or parameter of the disclosure should, unless the context indicates otherwise, be regarded as having been disclosed in combination with any and all other preferences, options particular features and the like as indicated for the same or other aspects, features and parameters of the disclosure.

The term "about" as used herein, e.g. when referring to a measurable value (such as an amount or weight of a particular component in the reaction mixture), refers to variations of ±20%, ±10%, ±5%, ±1%, ±0.5%, or, particularly, ±0.1% of the specified amount.

EXAMPLES

The present disclosure will be further described by reference to the following, non-limiting examples.

Example 1—Study into the Relationship Between Amlodipine Dose, Blood Pressure and Reported Side Effects The present study will investigate the tolerability of side effects and the relationship of these to the prescribed dose of amlodipine. It will measure the side effects of ankle swelling, headache and any other reported side effects using visual analogue scales.

The study will utilise a selection of questionnaires to investigate the relationship between patient beliefs about medicines and patients' adherence. The hypothesis of the study is that patients' tolerability of side effects (as measured by VAS) will be related to their beliefs about the necessity of medication (necessity concerns), their concerns about side effects and their adherence to medication.

This study will only look at doses within the current maximum licensed 10 mg dose (although higher doses are used in specialist clinics for selected patients).

Patients will be aged 18 years and over with no upper limit and, will all have had a diagnosis of essential hypertension by NICE/BIHS CG127 criteria with pre-treatment 24 h ABPM recording, or home readings pre-treatment. For inclusion in the poor BP control cohort recent home BP recordings including the 5 days' run-in period will average 140 mmHg or greater (SBP) and/or 90 mmHg and above (DBP). Patients will be receiving prescription drug treatment (minimum of one drug) to reduce blood pressure which may include amlodipine. Patients may have a prior history of unwanted effects on amlodipine.

Patients will have blood pressure measured by standard CE marked blood pressure measurement devices at home, using either their own device or a monitor provided to them for use in this study.

Amlodipine will be given in liquid form to facilitate achieving particular dosages in the pending development of a suitable solid dosage form. If inadequate blood pressure control is confirmed from home recordings averaging either systolic BP>=140 mmHg and/or diastolic BP>=90 mmHg, then based upon the PI or Sub-Investigator's and patient's agreement the patient will have amlodipine introduced or their amlodipine dose increased, milligram-by-milligram, from the baseline dose every 2 weeks. At each remote consultation review by the research clinic, at least every 2 weeks, the home blood pressure readings captured on the electronic diary and the patient's own e-diary reports of any adverse effects of treatment will be used as the basis of a discussion and decision about further dose escalation of amlodipine.

Amlodipine dosing will be titrated according to patient wanted and unwanted effects as reported via the digital diary. The diary will be reviewed by the clinician who will directly review it via the electronic database before making decisions on dose titration.

Patients will be closely monitored, with remote consultations with PI or delegate at least every two weeks and twice daily home blood pressure measurements and once daily recording on the e-diary of any unwanted effects. Each patient's GP will be notified via letter/email of their participation with the patient's permission.

The electronic diary in the patient's phone provides them with a graph and running average of their blood pressures over the last seven days, which is likely to make it easier for patients to relay blood pressure readings to healthcare professionals. The study is aiming to avoid increasing GP workload.

Figure 4:
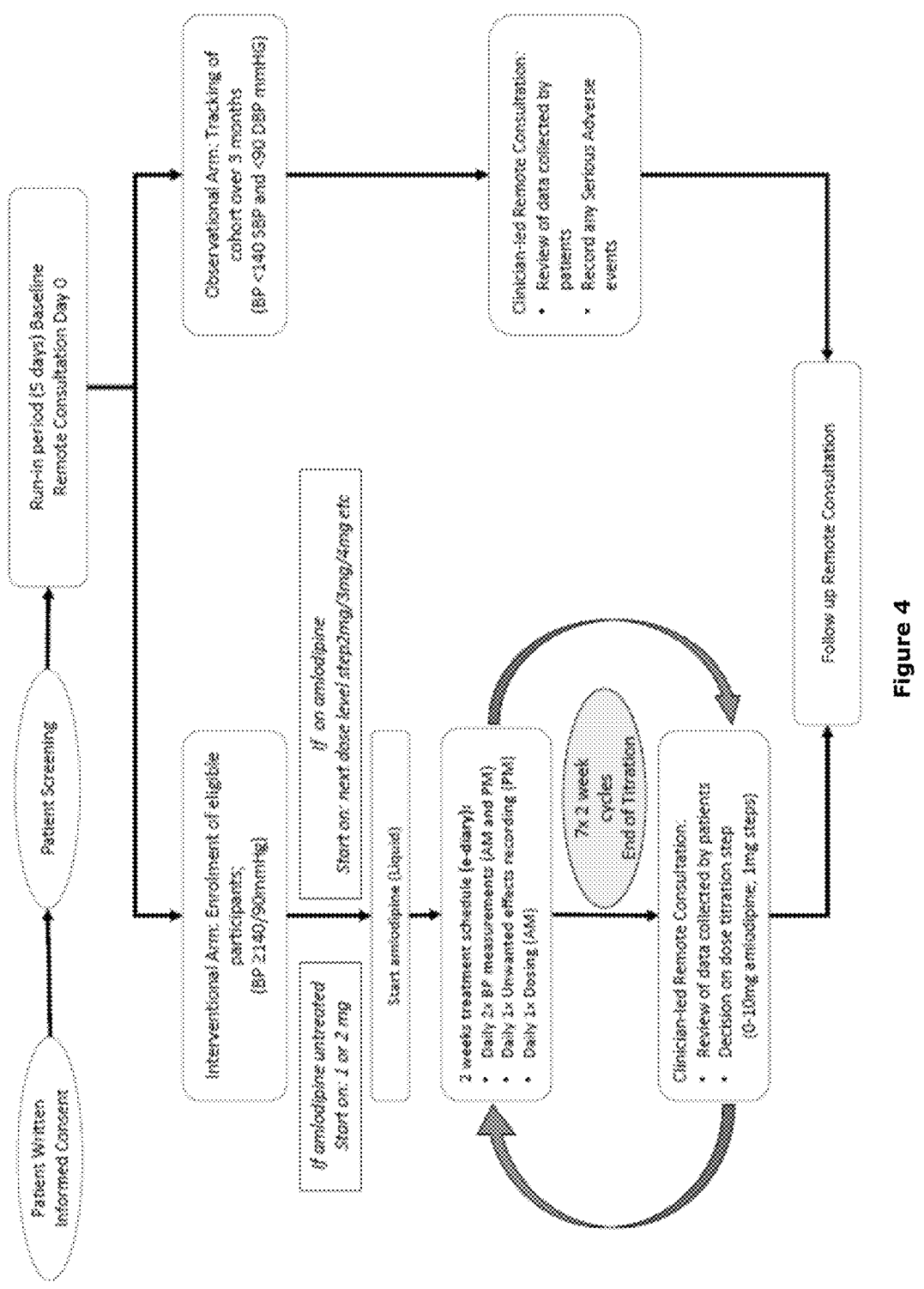
Figure 5:
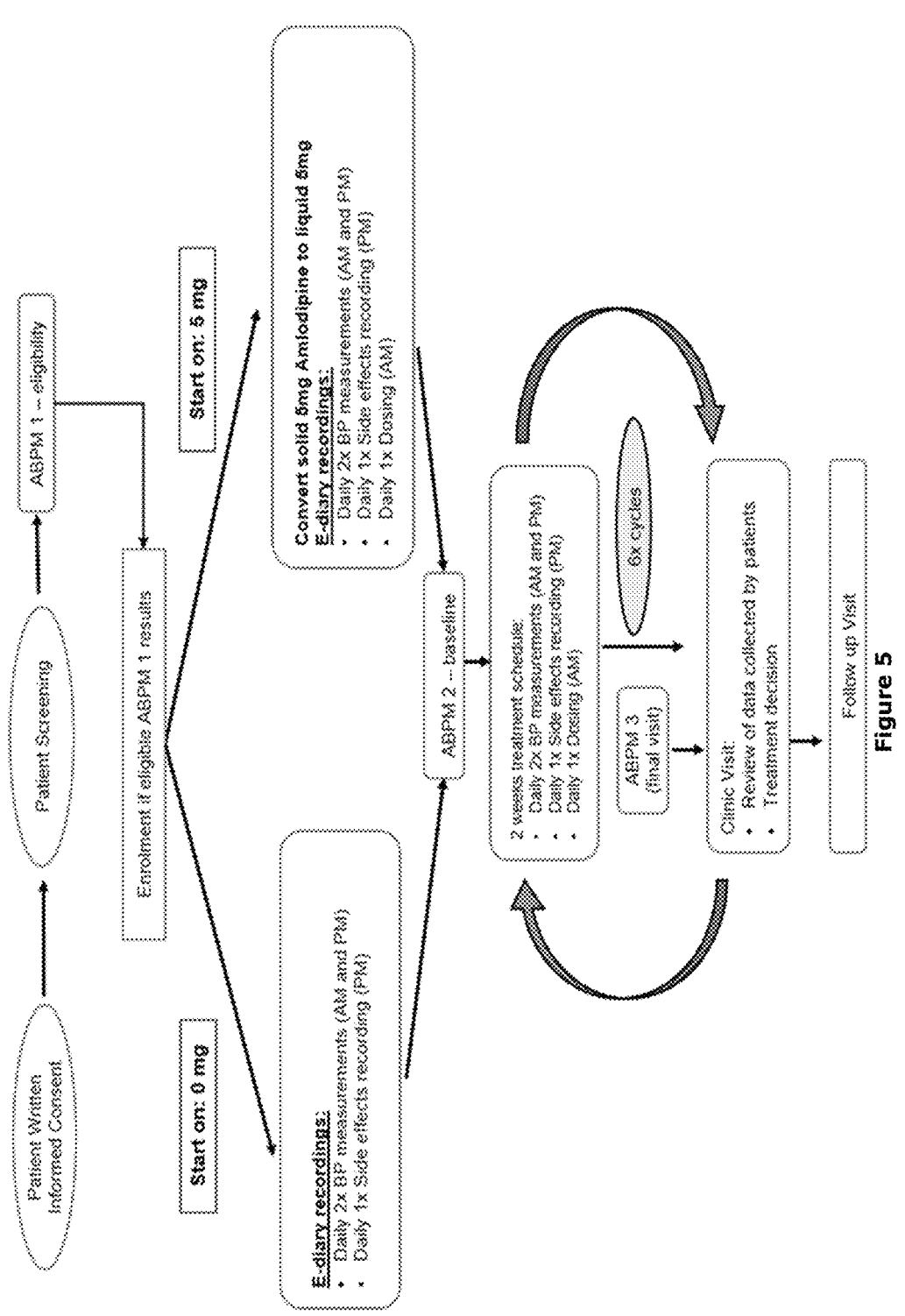

Flowcharts of the trial format is shown in FIGS. 4 and 5.

The primary objective of the study is to assess precision dosing of amlodipine to deliver reductions in blood pressure in patients with primary hypertension and inadequate BP control by up-titration of amlodipine in 1 mg or 2 mg increments under a remote medical management protocol.

Patients will be enrolled into the intervention part of the study who have:

Previous documented diagnosis of essential hypertension by NICE/BIHS CG127 criteria with pre-treatment 24 h ABPM recording, or home readings pre-treatment.

OR

Recent home BP recordings averaging above 140 mmHg (SBP) and/or 90 mmHg (DBP) obtaining during a 5 days run-in period.

Receiving prescription drug treatment (minimum of one drug) to reduce blood pressure. With an aim of optimally controlling their blood pressure through personalizing an amlodipine dose regimen (in 1-2 mg stepped intervals) and achieving a reduction in their home systolic blood pressure compared to baseline dose whilst minimizing unwanted side effects.

The change in home measured systolic blood pressure between baseline and at End of Treatment visit will be evaluated. Each patient will act as their own control.

Secondary objectives include:

Difference in home measured diastolic blood pressure between baseline and EOT.

Assess tolerability/side effects of study drug using a digital diary

Assess feasibility of collecting data using a digital diary.

Collect patient reported data including satisfaction with medication regime using digital diary and patient completed questionnaires on quality of life, beliefs about medicines and compliance.

Patient feedback on the use of digital diary at their last treatment consultation prior to their follow-up visit Insight into number of patients achieving target BP of <140 and/or <90 at EOT.

Insight into number of patients achieving reduction in systolic BP of ≥5 mmHg at EOT.

Insight into number of patients achieving reduction in systolic BP of ≥10 mmHg EOT.

Insight into number of patients achieving reduction in diastolic BP of ≥5 mmHg at EOT.

Assess ease of enrolling patients into a home BP monitoring study

Table 3 lists the Primary and secondary Objectives and Endpoints of the study.

| Primary Objective | Primary Endpoint | Outcome Measures |
|---|---|---|
| The primary objective of the study is to assess precision dosing of amlodipine to deliver reductions in blood pressure in patients with primary hypertension and inadequate BP control by up-titration of amlodipine in 1-2 mg increments. | Mean change in daily SBP (five day period of recordings approx. 30 values) | This will be measured from baseline to end of Treatment. Five day period at baseline To five day period at End of Treatment (EOT), aimed to be at optimal dose |

| Secondary Objective | Secondary Endpoint | Outcome Measures |
|---|---|---|
| Other clinically significant blood pressure measures which related to difference in measured blood pressure between baseline and EOS | Mean change in daily DBP | This will be measured from baseline to end of treatment (EOT). |
| Collect data on tolerability/ side effects | Reports of side effects using digital diary | This will be assessed using daily diary completion data |
| Collect patient reported outcome data Including satisfaction with medication regime using digital diary | Collection of Usability questionnaire to measure feasibility of data collection using digital diary | This will be measured using diary completion data and scales to review patient satisfaction from baseline to end of treatment (EOT). |
| Patient feedback on the use of digital diary | Collection of Usability questionnaire to assess user experience | Measured from baseline to end of treatment (EOT). |
| Parent's beliefs about medicines | Collection of data on patient's beliefs on taking medication | Beliefs about medicines (as measured by BMQ) from baseline to end of treatment |
| Patient's adherence to medication on a daily basis | Collection of data on the Extend of Adherence questionnaire, and the Making Medicines Work For You questionnaire to review adherence to taking medication | Adherence to medication from baseline to end of treatment |
| Patient's quality of life perception | Change in reported QoL | Quality of life (as measured by EQ5D) from baseline to end of treatment |

Remote consultations will be carried out by teleconference as pre-agreed between the PI or Sub-Investigator and the participant (via a video-capable device as a mobile phone, laptop, PC etc and associated application(s) such as Zoom, Facetime etc. or if that is not possible by audio/ telephone call).

As part of remote consultations, participants will be required to perform 3 blood pressure measurements while the PI (or delegate) observes them (where video-enabled consultation is possible) and record the values directly into patient's record either on paper which will then be transferred into the database, or directly into the electronic database.

Table 4 lists the Study Schedule.

| Schedule of Assessment Remote Consultation # | NAME | ACTIVITIES |
|---|---|---|
| 0 | PRE-SCREENING REMOTE CONSULTATION | Pre-screening form completed by direct care team via telephone (includes medical history, medication, home BP reading x3 if patient has own BP monitor, patient reported height, weight) Patient provided with PIS/ICF (postal or email) |
| 1 | SCREENING REMOTE CONSULTATION (DAY -5 to -7) Consultation may be completed in 2 parts to allow time for receipt of signed ICF by PI or delegate | Inclusion/Exclusion ICF Form signed (DocuSign or 'wet ink' hard copy) returned and then countersigned by clinician Patient assigned patient ID (six characters) Home BP review E-Diary download rising enrolment code (consultation may be paused to allow time for patient to complete download process). Patient trained on e-diary usage (record home BPs twice daily during the initial run-in period)) Home BP device dispatched to patient if applicable IMP shipped to patient if applicable |
| 2 | BASELINE REMOTE CONSULTATION Consultation to be completed in 2 parts to allow time for receipt of study drug by patient PART A DAY 0 (Day BP eligibility confirmed) | Home BP review E-diary reviewed (minimum of 5 consecutive day's complete twice daily BP recordings or SBP/DBP required ie Day -5 to Day -1) Review hypertension medication Eligibility confirmed by clinician Questionnaires completed (paper posted or/online as applicable) EQ5D BMQ EoA MMWFY |
| | PART B (first day of dosing with study drug = DAY N; to as dose as possible to Day 0 and no more than 5 days later) Day 1-5 | AFTER RECEIPT OF STUDY DRUG BY PATIENT Record Adverse events E-Diary: patient trained on additional/all features of e-diary (to record dose taken, home BPs twice daily and side effects). IMP: Patients to receive amlodipine 1-2 mg/day initially for those not currently receiving amlodipine; for those currently receiving amlodipine tablets to receive an increased dose (converted to liquid or adding liquid 1-2 mg to existing tablet dose) at the next step up in the sequence 3 mg, 4 mg, 5 mg. 6 mg, 7 mg, 8 mg, 9 mg, 10 mg/day. |
| 3 | DOSE TITRATION CONSULTATION 1 (Completion Treatment Week 1) DAY 7 +/− 2 | E-diary Printout reviewed by clinician Patients take home BP ×3 Review hypertension medication Record Adverse events IMP Dose Adjust/Dispense as applicable |
| 4 | DOSE TITRATION CONSULTATION 2 (Completion Treatment Week 2) DAY 14 +/− 2 | E-Diary Printout reviewed by clinician Review hypertension medication Patients take home BP ×3 Record Adverse events IMP Dose adjustment |
| 5 | DOSE TITRATION CONSULTATION 3 (Completion Treatment Week 4) Day 28 +/− 4 | E-Diary Printout reviewed by clinician Patients take home BP ×3 Review hypertension medication Record Adverse events IMF Dose adjustment |
| 6 | DOSE TITRATION CONSULTATION 4 (Completion Treatment Week 6) Day 42 +/− 4 | E-Diary Printout reviewed by clinician Patients take home BP ×3 Review hypertension medication Record Adverse events IMP Dose adjustment |

-continued

| Schedule of Assessment Remote Consultation # | NAME | ACTIVITIES |
|---|---|---|
| 7 | DOSE TITRATION CONSULTATION 5 (Completion Treatment Week 8) Day 56 +/− 4 | E-Diary Printout reviewed by clinician Patients take home BP ×3 Review hypertension medication Record Adverse events. IMP Dose adjustment/Return |
| 8 | DOSE TITRATION CONSULTATION 6 (Completion Treatment Week 10) Day 70 +/− 7 | E-Diary Printout reviewed by clinician Review hypertension medication Patients take home BP ×3 Record Adverse events IMP Dose adjustment/Return |
| 9 | DOSE TITRATION CONSULTATION 7 (Completion Treatment Week 12) Day 84 +/− 7 | E-Diary Printout reviewed by clinician Review BP, hypertension medication Record Adverse events Patients take home BP ×3 IMP Dose adjustment/Return |
| 10 | END OF TREATMENT CONSULTATION (EOT) (Completion Treatment Week 14) Day 98 +/− 7 | E-Diary Printout reviewed by clinician Patents take Home BP ×3 Review hypertension medication Patient Reported Weight Review Adverse Events Arrange IMP Return collection if possible E-Diary disabled in patient phone or switched to modified E-Diary for potential entry to observational study (subject to informed consent). Clinician to write to GP outlining conversion to post-study medication, post-study treatment plan. Questionnaires completed (paper/online as applicable) EQ5D BMQ EoA MMWFY Userbility |
| 11 | FOLLOW-UP CONSULTATION (within 2-4 weeks of End of Treatment) | Patients take Homs BPx3 Review BP Post-study treatment plan review Record Adverse events |

Trial Assessments

Patient assessments will be undertaken via remote consultations (teleconference) and through patient's completion of the e-Diary.

Screening Consultation

Consent will depend on the discussion of the desirability/patient willingness to try slowly ascending doses of amlodipine.

Patients will have one remote pre-screening consultation and one remote screening consultation during which informed consent is to be obtained.

Patients will have their clinical history documented, list of current medications including antihypertensive medications (and associated health effects). Their (self-reported) height and weight will be recorded and home measured blood pressures will be recorded. A standard clinic pre-screening form will be completed by a member of the direct care team and stored in the patient study files on site. A copy of the PIS and ICF will be posted to the patient's home address or emailed to them.

After receipt of signed ICF, this will be counter-signed by the PI or delegate ('wet ink' signature or DocuSign as applicable). Following confirmation of eligibility the patient will be instructed how to download the study e-Diary using an enrolment code and either wifi or a mobile data hotspot for the download.

The patient will be trained on the e-Diary (only to record home BPs twice daily during the initial run-in period). BP monitoring training will be given to patient. A home BP device will be dispatched to the patient (if patient does not already have a suitable device). BP monitoring training will be given to patient once they have received the device.

The patient will be requested to complete a minimum of 5 consecutive days of twice daily blood pressure readings immediately prior to conduct of the Baseline consultation (see below).

Re-Screening

At the clinician's judgement, the run-in period may be repeated once

Patients in the observational cohort, whose blood pressure rises during the study, may be approached to join the interventional cohort if they meet the entry criteria, at the discretion of the investigator.

Baseline Consultation

Eligibility for study participation will be confirmed during this visit. A minimum of 5 consecutive day's complete twice daily BP recordings of SBP/DBP required i.e. Day −5 to Day −1.

At the baseline consultation the patient will measure their BP (3 readings). The results will be reviewed with the clinician.

The Baseline consultation can be completed in 2 parts to allow time for receipt of study drug by patient. After receipt of study drug by patient, amlodipine starting dosage will be confirmed and patients will receive training in the dosing protocol. Patients will complete four paper/online questionnaires (EQ5D, BMQ, EoA, MMWFY). Adverse events will be reviewed.

Patients will receive refresher training in home blood pressure monitor use.

Study Consultations

Patients will have a remote consultation via teleconference at least every two weeks while on treatment (consultations 3-11) to have their blood pressure reviewed, digital diary data reviewed, adverse events reviewed, and medication dosage adjusted as indicated.

Compliance will be checked every two weeks by form of data entry and self-reported outcomes by the patient.

Questionnaires

Questionnaires will be completed by the patient at baseline and the end of treatment visits.

1. EQ-5D

The EuroQol-5 dimension quality of life measure is the most widely used generic health related quality of life questionnaire.

2. Beliefs about Medicines Questionnaire (BMQ) (Horne, Weinman & Hankins 1999)

This questionnaire is in two parts: the first part explores how people feel about the necessity of medicines in general (specific-necessity) and the second part their views on how their specific medications affect them (specific-concerns). These can be used separately or together. The specific-concerns construct contains both an emotional and cognitive component. The questionnaire has an 18-item, 4 factor structure. This questionnaire has been widely used across different patient groups including cardiac patients and has acceptable stability across illness groups.

3. Extent of Adherence Scale (Voils, 2012)

The Voils scale measures both the extent of nonadherence (3 items) and the reasons for it (21 items). Voils tool views adherence as a dual construct assessing extent of nonadherence (which provided reliable scores with alpha=0.84). Correlations with comparison measures and blood pressure were statistically significant and provided evidence of convergent, discriminant and concurrent validity. Reasons for nonadherence were examined by test-retest reliability (intraclass correlations). These were sufficiently small to indicate that items are measuring independent reasons for nonadherence.

4. Making Medicines Work for You (Weinman) (2019)

This screening tool has been designed to improve the identification of medical adherence and enable discussion of this in routine consultations. It is strongly correlated with the BMQ and the Morisky Medication Adherence Scale (MMAS 4) and has good sensitivity and specificity against these questionnaires. The questionnaire has 8 items and has been developed in consultation with patients and clinicians. It is easy and quick for patients to complete. The study will investigate the relationship between patient beliefs about medicines (using the Beliefs about Medicines Questionnaire BMQ) and their adherence using the Medication Adherence Questionnaire (Voils) and the Making Medicines Work for You MMWFY questionnaire (Weinman).

The hypothesis is that patients' tolerability of side effects (as measured by VAS) will be related to their beliefs about the necessity of medication (necessity concerns), their concerns about side effects and their adherence to medication. The patients who believe that the amlodipine is necessary and believe it will help them are more likely to adhere to the medication and tolerate the side effects. These patients will most likely obtain greater improvements in blood pressure.

5. User Experience Questionnaire (UEQ)

This will be completed once (at the end of treatment study visit), and it is a bespoke questionnaire designed to evaluate the patient's experience of the digital diary. Patients who withdraw from the study will be offered the questionnaire.

Follow Up Procedures

Patients will be followed-up with a post study visit 4 weeks after their end of treatment visit, with a window of −2/+4 weeks.

Clinic blood pressure and any adverse events will be recorded, and post study medication will be reviewed to ensure that patient is established on the post-study medication plan under the care of their GP.

Withdrawal Criteria

Patients can withdraw from the trial at any time, and without giving a reason.

The PI/CI can also withdraw a patient from the study for any of the following reasons:

1. Any concurrent illness that prevents further treatment.

2. Any change in the patient's condition that justifies the discontinuation of treatment in the clinician's opinion.

3. Any other reasons the subject cannot adhere to study visits or procedures.

4. Persistent non-compliance

Withdrawal of a Patient from the Treatment Part of the Study Prematurely—

Safety follow up will be continued until the patient's blood pressure is stabilized and the patient will be established back to the care of their responsible HCP. If the patient is withdrawn during the treatment (titration) stage of the study, they will be offered the study questionnaires for completion.

If a patient withdraws from the study prior to completion of dose titration consultation 1, another patient will be enrolled to replace them. Patients who are enrolled but withdraw will not have their medical care affected and return to standard clinical care.

Early Withdrawal Procedure

Withdrawal of a patient from the study would, subject to the patient's consent, will always be followed by an End of Study visit at which any adverse events, home blood pressure records, self-assessments of unwanted effects of drug on the e-diary, clinic blood pressure measurements and any clinically relevant safety checks (physical examination, blood tests, if required to provide good care to the patient) will be recorded.

If patients stop taking a study medication, the clinician provides the equivalent follow-up until the projected final visit date (if the patient wishes) to ensure that clinical care is not conditional on taking the medication.

A follow-up visit after the study will always be offered to ensure that the patient is stable and settled back on either their pre-study regime or an alternative plan agreed with GP and study team at the end of study visit.

The investigator will make the decision as to when persistent non-compliance will result in the patient being withdrawn. Other reasons to withdraw the patient also include persistent non-attendance for clinic visits. Non-compliant patients will be followed-up by telephone by research/clinic staff who will make three attempts via telephone or email to contact the patient requesting compliance or arranging a non-study visit, before marking them as withdrawn.

End of Treatment Visit

During the EoS consultation, the clinician will review the results of the blood pressures, side effects, record adverse events, and note the patient's (self reported) weight. The patient will be asked to delete the e-diary from their smartphone. The clinician will confirm the post-study treatment plan, including what medication the patient will be converted to. The patient will be asked to complete four questionnaires.

End of Trial (EOT) Definition

The EOT definition for this study will be the last visit of the last patient.

The CI is delegated the responsibility of submitting the EOT notification to REC and MHRA once reviewed by sponsor. The EOT notification must be received by REC and MHRA within 90 days of the end of the trial definition being met. If the study is ended prematurely, the CI will notify the Sponsor, REC & MHRA including the reasons for the premature termination (within 15 days).

Laboratories and Samples

There are no samples scheduled to be taken in this study for laboratory analysis.

Trial Medication

Name and description of investigational medicinal product(s)

The trial medication is Amlodipine 1 mg/ml Oral Solution. This is an oral solution. Each ml contains 1 mg of amlodipine (as besilate).

For both hypertension and angina the usual initial dose is 5 mg (5 ml) of amlodipine once daily which may be increased to a maximum dose of 10 mg (10 ml) depending on the individual patient's response. The medication is stored in an Amber bottle (Type III glass), with a child-proof closure. This medication is administered orally, using the manufacturer-supplied dosing syringe. One bottle contains 150 ml.

Legal Status of the Drug

The medication is licensed for use: PL 00427/0234. The trial is being carried out under a Clinical Trial Authorisation (CTA). The drug is therefore only to be used by the named investigators, for the participants specified in this protocol, and within the trial.

Summary of Product Characteristics (SmPC)

A Summary of Product Characteristics (SmPC) for amlodipine will be used for this trial.

Drug Supply and Storage

Amlodipine will be procured and stored by Barts Health Pharmacy (St Bartholomew's Hospital dispensary). To facilitate the study, the pharmacy location will hold small batches of the medication. This will be located within the WHCRC. It will be stored in a temperature monitored refrigerator (2-8° C.), within the laboratory at the WHCRC, in its original package. The shelf life of an unopened bottle is 1 year. Once opened, it must be used within 30 days. The bottle should be stored upright and in the refrigerator.

Manufacturer

Amlodipine is manufactured with a marketing authorisation number: PL 00427/0234.

Dosage Schedules

Liquid amlodipine will be taken by the patient, once each day, in the morning, just after home blood pressure recordings are completed. The dose will be prescribed by the study doctor, initially beginning at either 0 mg or 5 mg and documented in the patient study files dose increments will be made at each visit until an optimal balance between stable blood pressure and minimal side effects is achieved by week 14.

Patients will draw up the correct dose of amlodipine liquid from the bottle, using a graduated syringe for ease of use.

The maximum licensed dose of Amlodipine and for the study purpose is 10 mg. In case of ingesting more than 10 mg/day in error, the patient is required to contact the clinical team so a course of action can be provided.

Dispensing of IMP

Amlodipine will be dispensed by the direct are team under the guidance of the BH Trust pharmacy service, using the subsidiary dispensary at WHCRC. An accountability log will be completed for each dispensing. Patient files will also be updated to document patient receipt of amlodipine. IMP will be posted or couriered to the patient. Both the WHCRC and laboratory at St. Barts hospital have standard operating procedures for storage that cover IMP management including temperature monitoring, calibration of temperature recording devices, storage and when necessary postage/courier despatch of the IMP.

Dosage Modifications

Any treatment breaks should be documented and minimized. Incomplete dosing may lead to extension of time between dose adjustments. The treatment break will be based on drug tolerability as assessed in study consultations. Treatment breaks of up to 3 weeks will be permitted based on drug tolerability or patients request due to valid reason in the opinion of the PI or Sub-Investigator. This will be documented in the patient study files.

Dose modifications will be at the discretion of the PI or Sub-Investigator based on blood pressure readings and side effects in keeping with the study's primary objectives (Section 11.6).

Known Drug Reactions and Interaction with Other Therapies

All known drug reactions and interactions with other therapies are outlined in Section 4.5 of the SmPC for Amlodipine 1 mg/ml Oral Solution (12 Feb. 2018).

Prior and Concomitant Medication

During the study consumption of excessive quantities of foodstuffs which may alter the absorption/metabolism and/or effects of amlodipine, such as grapefruit, will be discouraged.

All other blood pressure lowering drugs are permitted, providing their doses can remain stable for the duration of the study (allowing for unexpected changes for patient safety, of course).

Trial Restrictions

Amlodipine is contraindicated in patients with:

Hypersensitivity to dihydropyridine derivatives, amlodipine or to any of the excipients.

Severe hypotension.

Shock (including cardiogenic shock).

Obstruction of the outflow tract of the left ventricle (e.g., high grade aortic stenosis).

Haemodynamically unstable heart failure after acute myocardial infarction.

Assessment of Compliance

Compliance will be monitored by reviewing the patient data entry in the digital diary.

The clinician will monitor IMP compliance as per patient's diary entry and confirm patient's continuance on the trial. Non-compliance to the protocol study procedures will be documented by the investigator in the patient study files and reported on the electronic database.

Name and Description of Each Non-Investigational Medicinal Product (NIMP)

There are no NIMPS in this trial.

Arrangements for Post-Trial Access to IMP and Care

Safety follow-up will be continued as is agreeable to the patient until blood pressure is stabilized, and the patients is established back in the care of their GP Equipment and Devices

| | |
|---|---|
| Omron Blood Pressure Monitor (where issued to patient without home BP machine) | Manufacturer: Omron Healthcare Europe<br>Indication: Measuring blood pressure<br>CE Mark: 0197<br>Source of Device: Devices will be purchased prior to trial opening, as part of the trial.<br>How device is used: Device is standard care. Omron M3 Upper Arm BPM (HEM-7155-E) . It is 4 AA batteries or optional AC powered. The wide-range cuff provided supports a wide range of arm sizes to 42 cm and up to 50 cm (XL size). The patient puts on the cuff following instructions that came with the monitor. Three readings are taken (usually two minutes apart). Readings are displayed on the screen. The patient will transfer the readings from the device to the electronic dairy app on their mobile phone.<br>Device and equipment custodian: The device will be made available to each patient by CLM via WHCRC. Devices will be calibrated by manufacturers. As per SOP 020 (Use and Maintenance of equipment), devices are serviced annually per device instructions by research staff. A record will be kept logging which blood pressure monitor has been provided to which patient. Patients will be gifted the home blood pressure monitors to retain at the end of the study |

Statistical and Data Analysis

Sample Size Calculation

Calculations assume a change of 4 mmHg/3 mmHg from baseline, and standard deviation of blood pressure change of 8.7 mmHg for SBP and 6.3 mmHg for DBP.[2]

The following numbers would be required to be able to detect the specified change within patients at the 5% significance level.

| | SBP Power | |
|---|---|---|
| Change in blood pressure | 80% | 90% |
| 4 mmHg | N = 62 | N = 82 |
| 3 mmHg | N = 108 | N = 144 |

Primary Outcome Analysis

Hypothesis testing of the primary endpoint will be carried out at the 5% (2-sided) significance level. All confidence intervals presented will be 95% and 2-sided.

The mean BP will be calculated for each patient. Mean values (SD) will be shown at baseline and post-titration (14 weeks). A paired t-test will be conducted and the mean change from baseline to 14 weeks (95% CI) and p values will be calculated.

Figure 6:
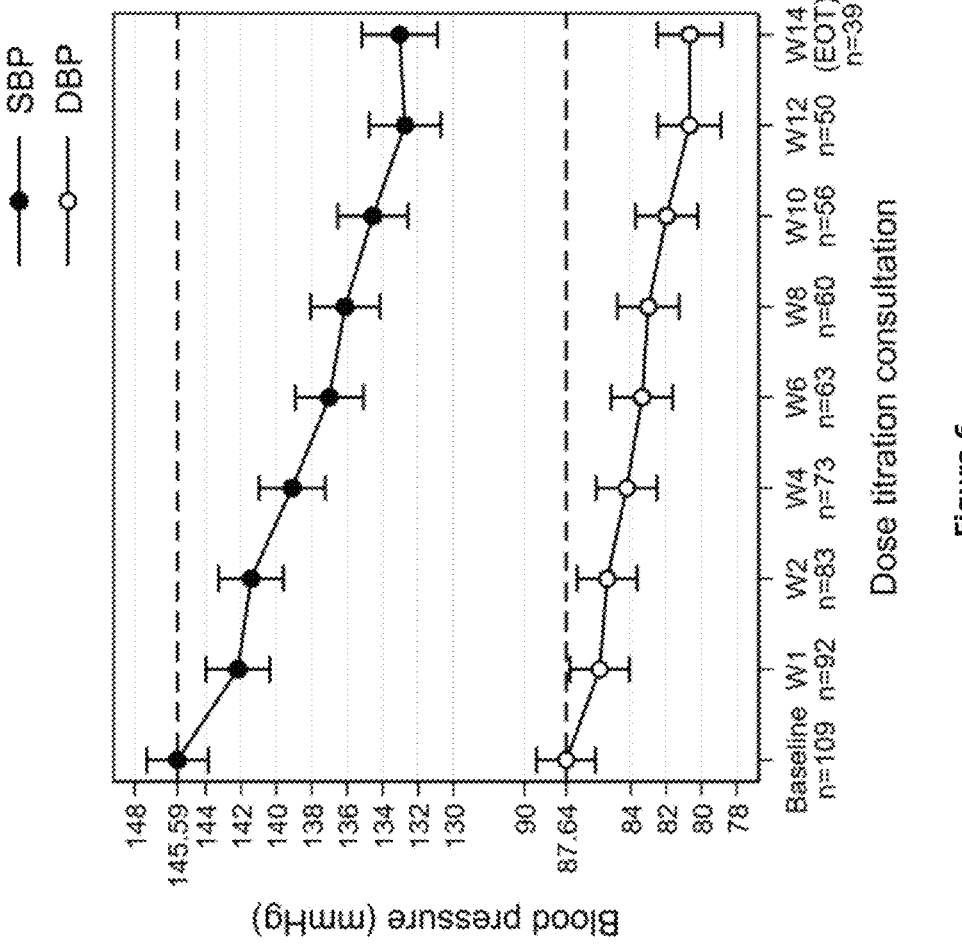

Normality of the change variable will be assessed using quantile-quantile plots and histograms and the occurrence of outliers will be identified. If the model assumptions are not met the analysis will be repeated using a non-parametric test (Wilcoxon signed-ranks). Subgroup analysis will be performed for the primary endpoint stratified by initial dose (0 mg or 5 mg) and by use of other blood pressure lowering medication vs. amlodipine alone. Analysis will be undertaken on all enrolled patients and on a per protocol population Secondary Outcome Analysis Analysis of secondary endpoints will be descriptive. For all continuous secondary endpoints, mean (SD) will be shown at each time point and the change (95% CI) will be estimated. For categorical secondary endpoints the number and proportion will be shown. In addition mediation analysis will be undertaken using questionnaire data to estimate the direct and indirect effects of beliefs about Trial Results To date, 109 patients (n) have begun the trial with 39 of them having completed it. The graph in FIG. 6 shows the estimated mean blood pressure (95% CI) at each dose titration consultation. The estimates are from linear mixed model for longitudinal data with random subject effect and are based on accumulating data. The mean blood pressure baseline at the beginning of the study was found to be:

SBP=146 mmHg

DBP=88 mmHg

As shown in FIG. 6, both the SBP and DBP reduced with each small dose change until the end of the study. The end mean SBP and DBP were found to have been reduced to:

SBP=133 mmHg

DBP=81 mmHg

Furthermore, no toxic related side effects leading to treatment discontinuation were observed during the trial to date.

Figure 7A:
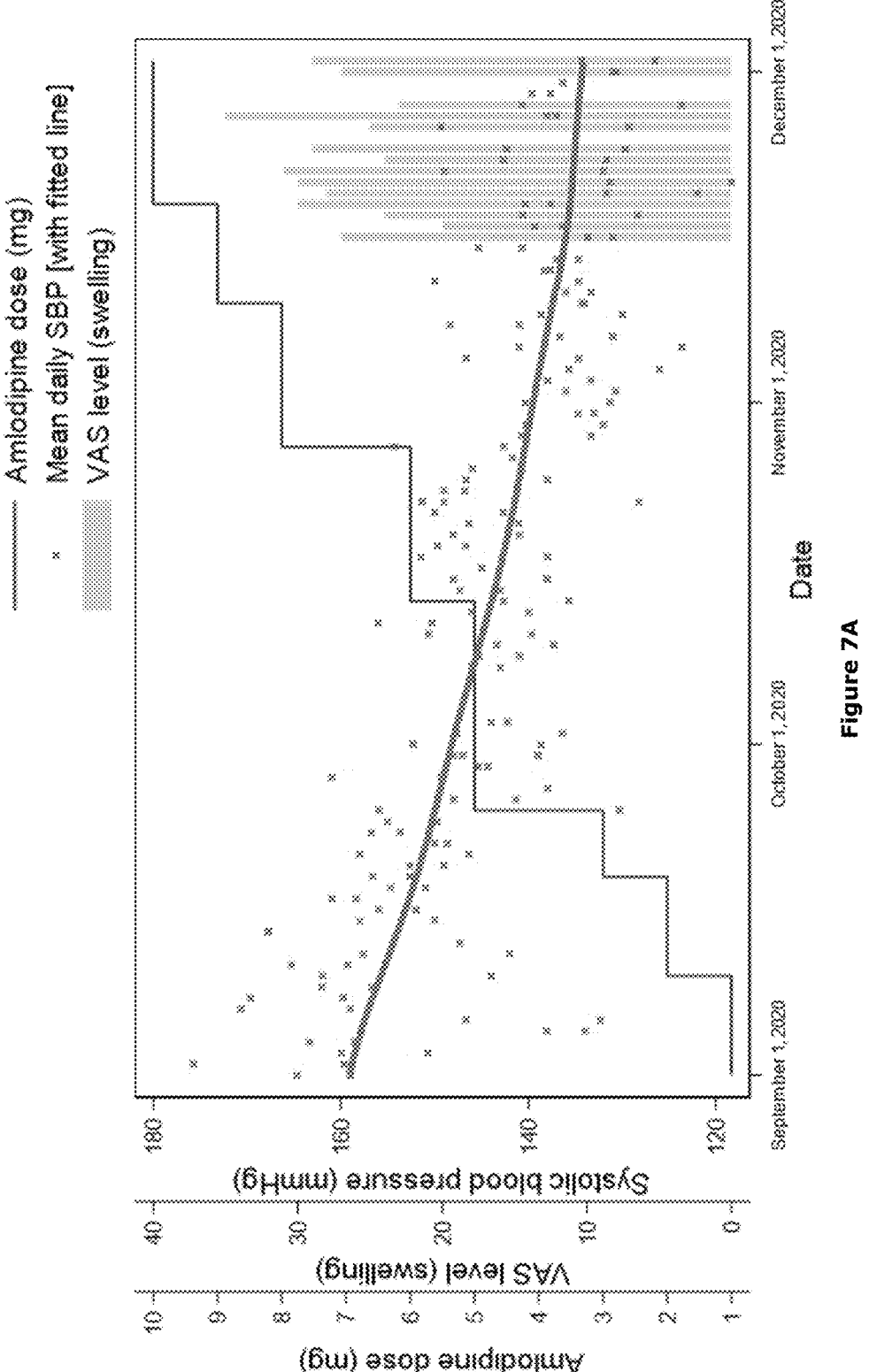
FIGS. 7A and B. VAS level and SBP (FIG. 7A) or DBP (FIG. 7B) vs dose titration graph from an individual patient in the exemplary trial
Figure 7B:
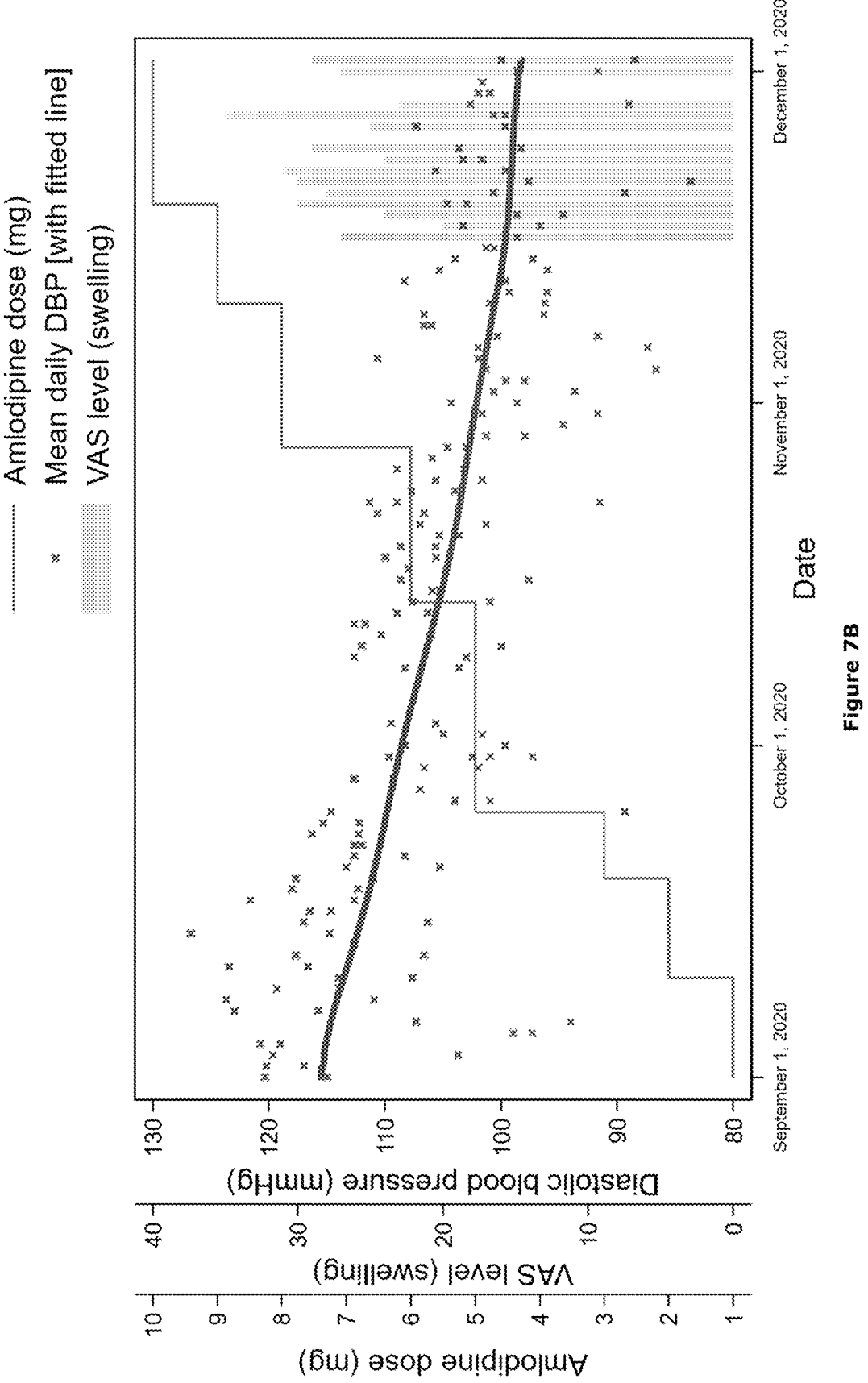

FIGS. 7A (SBP) and 7B (DBP) show points from a single patient who has completed the study. The results show that as the dose increases incrementally, blood pressure falls and at the higher doses the side effect, oedema, emerges as measured by the VAS level. VAS is a 0-100 scale (categorised as: 0 is no side-effect, 1-25 is mild, 26-50 is moderate, 51-75 severe, and 76-100 is very severe). As shown in the Figures, the VAS scores obtained indicate that side effects were mild to moderate at a final dose of 10 mg (which is a standard dose) and the decision for long term treatment could be at non-standard (rather than standard) dose e.g. 9 mg and with the potential for no or mild side effects based on these data. Furthermore, the emergence of the side effects occurred over a narrow dosage change. This shows that the dosage regimen has been able to maximise the lowering of the patient's blood pressure whilst minimising the side effects induced. The blood pressure readings also show the variability in a small time frame (e.g. within a single day or two days) and hence the value gained from the dosage regimen's regular monitoring and using a moving average blood pressure value in the regimen.

The trial results therefore demonstrate that the disclosure's dosage regimen involving precision dosing of amlodipine can deliver reductions in blood pressure in patients with hypertension yet minimise side effects. The relationship between dose, blood pressure and side-effects may be used to provide information on a proposed dosage regimen and makes it possible to both reduce side effects and better control blood pressure in the patient.

REFERENCES

Amlodipine Patient Insert Leaflet NDA 19-787/S-042
Donnelly R; Meredith P; Miller S; Howie C; Elliott H Pharmacodynamic modelling of the antihypertensive response to amlodipine: Clin Pharm Therap (1993)303-310
FDA Amlodipine Approval Clinical Pharmacology and Biopharmaceutical Review (2002): NDA 19-787/S30
Heo Y; Holford N; im K; Son Y; Park K, Quantitative model for the blood pressure lowering interaction of valsartan and amlodipine: Br J Clin Pharmacol (2016) 82 1557-1567 1557
Williams D; Cubeddu L; Amlodipine Pharmacokinetics in Healthy Volunteers, J CLin Pharm (1988) 28; 990-994

The invention claimed is:

1. A method for treating hypertension in a patient with a dosage regimen, wherein the dosage regimen comprises:
  i. for a period of from about 7 days to about 14 days:
    a) administering an initial daily dose of 1 to 10 mg amlodipine to the patient;
    b) recording patient's blood pressure readings on at least 3 separate days, using a blood pressure device;
    c) recording any side-effects experienced by the patient on at least 3 separate days;
  ii. increasing or decreasing the daily dose of amlodipine by between 1 mg and 2.5 mg, or maintaining the daily dose of amlodipine, based on the blood pressure readings and the patient reported side-effects; and
  iii. repeating steps (i) and (ii) with either the increased, decreased or maintained daily dose replacing the initial daily dose in step (a) for a number of times until a specified patient treatment period has elapsed or until a target blood pressure is reached.

2. The method according to claim 1, wherein step b) includes a determination of a moving average of the blood pressure readings and the increasing, decreasing or maintaining the daily dose in step (ii) is based on the moving average of the blood pressure.

3. The method according to claim 2, wherein the moving average is a 3-day moving average, wherein the days are consecutive.

4. The method according to claim 1, wherein the period in step (i) is either pre-determined or is determined by the time taken to reach less than 10% variability in the moving average blood pressure.

5. The method according to claim 1, wherein the blood pressure readings are recorded at least every other day.

6. The method according to claim 1, wherein blood pressure readings are recorded at the same time each day.

7. The method according to claim 1, wherein the patient's initial daily dose is determined based on their medical history and/or history of prior side-effects when taking amlodipine.

8. The method according to claim 1, wherein the patient's initial daily dose is determined by a physician or delegated health care professional.

9. The method according to claim 1, wherein the patient's initial daily dose is 1 mg, 2 mg, 2.5 mg, 3 mg, 4 mg, 5 mg or 6 mg.

10. The method according to claim 1, wherein the patients are selected for treatment if the patients have had a diagnosis of hypertension according to NICE/BIHS CG127 criteria, and wherein the patients have already had conducted 24h ambulatory blood pressure monitoring (ABPM) recording or home blood pressure monitoring.

11. The method according to claim 1, wherein the increasing or decreasing is in an increment of 1 mg, 2 mg or 2.5 mg.

12. The method according to claim 1, wherein the increasing or decreasing in step (ii) includes a comparison of the blood pressure with a control blood pressure and/or a dose/response curve for amlodipine personalised for the patient.

13. The method according to claim 1, wherein step (ii) is carried out by a physician or delegated health care professional or wherein step (ii) is carried out by software executed on an electronic device.

14. The method according to claim 1, wherein the recording of blood pressure is onto an electronic device.

15. The method according to claim 14, wherein data are transferred from the blood pressure device to the electronic device electronically and automatically.

16. The method according to claim 1, wherein the modification of the dose in step (ii) is based on patient tolerability of the side-effects.

17. The method according to claim 1, wherein the side-effects recorded by the patient are selected from the group consisting of one or more of swollen ankles, feet, and legs.

18. The method according to claim 1, wherein the side-effects recorded by the patient include hypotension.

19. The method according to claim 1, wherein the side-effects recorded by the patient include hypotension and one or more selected from the group consisting of swollen ankles, feet, and legs.

20. The method according to claim 1, wherein the recording of the side-effects is carried out daily.

21. The method according to claim 1, wherein the amlodipine is administered in solid form and via the oral route.

22. The method of claim 1 comprising recording the patient's blood pressure on at least 3 separate days and calculating a moving average of the blood pressure and producing an amlodipine dosage regimen based on the moving average of the blood pressure readings and the patient reported side effects.

* * * * *